(12) United States Patent
Lee et al.

(10) Patent No.: US 9,220,738 B1
(45) Date of Patent: Dec. 29, 2015

(54) HERBAL COMPOSITION AND A METHOD OF TREATING UTERINE FIBROIDS

(71) Applicant: KANG LI BIOTECH CO., LTD., Kaohsiung (TW)

(72) Inventors: Shih-Chiang Lee, Kaohsiung (TW); Shorong-Shii Liou, Kaohsiung (TW); I-Min Liu, Kaohsiung (TW); Chia-Ru Chang, Kaohsiung (TW)

(73) Assignee: Kang Li Biotech Co., Ltd., Kaohsiung (TW)

( * ) Notice: Subject to any disclaimer, the term of this patent is extended or adjusted under 35 U.S.C. 154(b) by 0 days.

(21) Appl. No.: 14/324,768

(22) Filed: Jul. 7, 2014

(51) Int. Cl.
| | |
|---|---|
| *A61K 36/06* | (2006.01) |
| *A61K 36/00* | (2006.01) |
| *A61K 36/54* | (2006.01) |
| *A61K 36/533* | (2006.01) |
| *A61K 36/07* | (2006.01) |
| *A61K 36/481* | (2006.01) |

(52) U.S. Cl.
CPC .............. *A61K 36/533* (2013.01); *A61K 36/07* (2013.01); *A61K 36/481* (2013.01)

(58) Field of Classification Search
None
See application file for complete search history.

(56) References Cited

U.S. PATENT DOCUMENTS

2006/0251581 A1   11/2006   McIntyre et al.

*Primary Examiner* — Chris R Tate
*Assistant Examiner* — Russell Fiebig
(74) *Attorney, Agent, or Firm* — Muncy, Geissler, Olds & Lowe, P.C.

(57) ABSTRACT

The invention discloses an herbal composition of treating uterine fibroid. The herbal composition comprises *Antrodia cinnamomea*, *Astragalus membranaceus*, and *Leonurus japonicus*; wherein the weight percentages of *Antrodia cinnamomea*, *Astragalus membranaceus* and *Leonurus japonicus* are 25 to 75%, 20.8 to 62.5% and 4.2 to 12.5% by weight of the formula, respectively. The invention also discloses a method of treating uterine fibroid.

2 Claims, 1 Drawing Sheet
(1 of 1 Drawing Sheet(s) Filed in Color)

HERBAL COMPOSITION AND A METHOD OF TREATING UTERINE FIBROIDS

BACKGROUND OF THE INVENTION

1. Field of the Invention

The present invention generally relates to an herbal composition and, more particularly, to an herbal composition of treating uterine fibroids. The present invention further relates to a method of treating uterine fibroids.

2. Description of the Related Art

A uterine fibroid is a leiomyoma that originates from the myometrium of the uterus. Uterine fibroids are the most common tumors in females typically found during the middle and later reproductive years. Most uterus fibroids are asymptomatic. However, as uterine fibroids grow, they may cause painful menses, abnormal gynecologic hemorrhage, and even infertility. In general, uterine fibroids can be removed by uterine myomectomy.

Most conventional drugs for uterine fibroids are drugs for improving symptoms of uterine fibroids. For instance, NSAIDs (non-steroidal anti-inflammatory drugs) are used to reduce painful menses. OCPs (oral contraceptive pills) are used to reduce uterine bleeding. On the other hand, GnRH (gonadotropin-releasing hormone) analog administration causes temporary regression of uterine fibroids by decreasing estrogen levels. However, long-term administration of GnRH analogs could lead to osteoporosis or postmenopausal symptoms. Moreover, in many cases, the uterine fibroids will regrow after cessation of treatment. Therefore, only the particular patients are recommended for GnRH analogs treatment.

In light of this, it is necessary to provide an herbal composition and a method of treating uterine fibroids.

SUMMARY OF THE INVENTION

It is therefore the objective of this invention to provide an herbal composition for inhibiting growth of uterine fibroids.

It is another objective of this invention to provide a method of treating uterine fibroids, with active ingredients extracted from the herbal composition, improving symptoms of uterine fibroids.

One embodiment of the invention discloses an herbal composition of treating uterine fibroids comprising: *Antrodia cinnamomea*, *Astragalus membranaceus*, and *Leonurus japonicus*; wherein the weight percentages of *Antrodia cinnamomea*, *Astragalus membranaceus* and *Leonurus japonicus* are 25 to 75%, 20.8 to 62.5% and 4.2 to 12.5% by weight of the formula, respectively.

In a preferred form shown, the weight percentages of *Antrodia cinnamomea*, *Astragalus membranaceus* and *Leonurus japonicus* are 75%, 20.8% and 4.2% by weight of the formula, respectively.

The other embodiment of the invention discloses a method of treating uterine fibroids, by administering an herbal extract to a subject in need thereof to suppress uterine fibroid. The herbal extract is manufactured as following: providing the herbal composition mentioned above; blending the herbal composition with a 95% ethanol solution with a weight-volume percentage being 50%, followed by extracting at 50 to 80° C. to obtain a herbal solution; and concentrating the herbal solution to obtain the herbal extract. Moreover, *Antrodia cinnamomea* is selected from fruiting bodies, *Astragalus membranaceus* is selected from roots, and *Leonurus japonicus* is selected from ground portions.

In another preferred form shown, the herbal extract is administered to the subject in need thereof in a dosage of 300 mg/per kilogram of body weight per day for 28 days.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention will become more fully understood from the detailed description given hereinafter and the accompanying drawings which are given by way of illustration only, and thus are not limitative of the present invention, and wherein.

Figure 1:
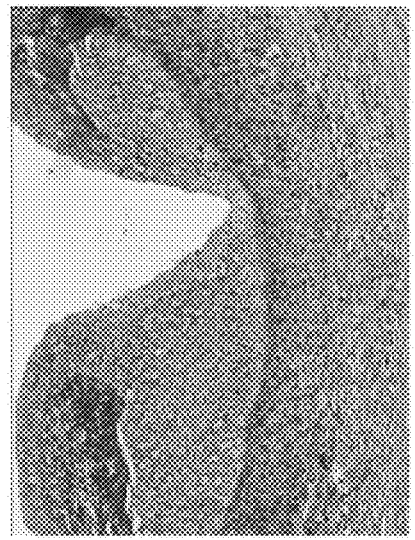
FIG. 1 depicts an H&E staining result of uterus obtained from group C0 rat.

In the various figures of the drawings, the same numerals designate the same or similar parts. Furthermore, when the term "first", "second", "third", "fourth", "inner", "outer", "top", "bottom" and similar terms are used hereinafter, it should be understood that these terms refer only to the structure shown in the drawings as it would appear to a person viewing the drawings, and are utilized only to facilitate describing the invention.

DETAILED DESCRIPTION OF THE INVENTION

An herbal extract according to preferred teachings of the invention comprises: *Antrodia cinnamomea*, *Astragalus membranaceus* and *Leonurus japonicus*. The herbal composition poses effects on inhibiting growth of uterine fibroids.

In detail, in the embodiment, the weight percentages of *Antrodia cinnamomea*, *Astragalus membranaceus* and *Leonurus japonicus* are 25 to 75%, 20.8 to 62.5% and 4.2 to 12.5% by weight of the formula, respectively. Preferably, the weight percentages of *Antrodia cinnamomea*, *Astragalus membranaceus* and *Leonurus japonicus* are 75%, 20.8% and 4.2% by weight of the formula, respectively. Accordingly, by the synergistic effect of several active ingredients provided from the herbal composition, growth of uterine fibroids is suppressed, and symptoms of uterine fibroids, such as painful menses and bleeding, are improved.

Moreover, *Antrodia cinnamomea* is selected from fruiting bodies of petri dish-cultured *Antrodia cinnamomea* rich in triterpenes. *Astragalus membranaceus* is selected from dried roots of *Astragalus membranaceus* (Fisch.) Bge. Var. *mongholicus* (Bge.) Hsiao or *Astragalus membranaceus* (Fisch.) Bge. rich in glycosides, polysaccharides, flavonoids, amino acids and micronutrients. *Leonurus japonicus* is selected from ground portions of *Leonurus japonicus* rich in alkaloids (such as leonurine, leonuridine, stachydrine), benzoic acid, potassium chloride, lauric acid, linolenic acid, oleic acid, vitamin A and flavonoids.

The herbal composition of the invention can effectively suppress growth of uterine fibroids, thereby being potential to be applied to pharmaceutical industry, being an active substance of medication or health products of treating uterine fibroids. In the present invention, an herbal extract extracted from the herbal composition of the invention can be given to any target individually or combined with any acceptable excipients, for example carriers or other ingredients, and is capable of being further manufactured into any form of medicament, such as pill, capsule, powder, solution and pastil for easy and convenient delivery to targets.

Preferably, the herbal extract is manufactured as following: providing the herbal composition mentioned above, extracting the herbal composition with a 95% ethanol solution at 50 to 80° C. for 8 to 12 hours to obtain an herbal solution, and concentrating the herbal solution to obtain the herbal extract.

In detail, the herbal composition is blended with the 95% ethanol solution with a weight-volume percentage being 50%, allowing the active ingredients of the herbal extract dissolving into the 95% ethanol solution. In the embodiment, 500 grams of the herbal composition is provided. 1 liter of the 95% ethanol solution is used to extract the herbal composition at 60° C. for 10 hours. The extraction process is repeated for 3 times.

The concentrating process of the embodiment is vacuum filtrated, vacuum concentrated, and followed by freeze-drying. After the concentrating process, the herbal extract is obtained.

Furthermore, the herbal extract can be administered to a subject in need thereof to suppress uterine fibroids. For example, the herbal extract can be administered to the subject in need thereof in a dosage of 300 mg/per kilogram of body weight per day for 28 days. Therefore, the active ingredients extracted from the herbal composition poses synergistic effect in the subject in need thereof, inhibiting the growth of uterine fibroids.

In order to evaluate the active ingredients extracted from the herbal composition of the invention comprises triterpenes and polysaccharides, and to further verify the herbal extract of the invention poses ability of inhibition growth of uterine fibroid, trials (A) to (C) are performed as following.

Trial (A): Contents of Active Ingredients

Referring to Table 1, 500 grams of the herbal compositions (with different amount of *Antrodia cinnamomea*, *Astragalus membranaceus* and *Leonurus japonicus*) are used in trial (A). The herbal compositions are extracted by 1 liter of the 95% ethanol solution, respectively. The resulted product are further filtrated, vacuum concentrated, followed by freeze-drying to obtain the herbal extracts of groups A1 to A3. Following trials with the herbal extracts are carried on.

TABLE 1

Herbal extracts used in trial (A)

| Groups | Amounts (g) | | |
|---|---|---|---|
| | Antrodia cinnamomea | Astragalus membranaceus | Leonurus japonicus |
| A1 | 250 | 208.5 | 41.5 |
| A2 | 125 | 312.5 | 62.5 |
| A3 | 375 | 104 | 21 |

Moreover, 0.2 grams of the herbal extracts shown in Table 1 are ultrasonic vibrated with 5 mL of methanol for 15 minutes, followed by centrifugation at 3,000 rpm for 10 minutes. 5 mL of supernatants are collected into new tubes, followed by heating with 100° C. water bath to dry.

For analyzing triterpenes, Purospher STAR (purchased from Merck) RP-18e (5 μm) 250 mm×4 mm column is used. A mobile phase is acetonitrile and 0.085% phosphoric acid mixed in a volumetric ratio of 47:53. A flow rate of the mobile phase is 1 mL/min. The percentages of the total triterpenes is calculated and shown in Table 2.

TABLE 2

Contents of active ingredients of herbal extracts in trial (A)

| Groups | Triterpenes (%) | Polysaccharides (ppm) |
|---|---|---|
| A1 | 22.34 ± 2.46 | 30.42 ± 3.72 |
| A2 | 16.63 ± 3.12 | 20.18 ± 2.96 |
| A3 | 26.74 ± 2.82 | 41.23 ± 3.87 |

Next, for analyzing polysaccharides, a standard curve is prepared with different concentrations of galactose. The herbal extract (1 mL) in Table 1 mixes with phenol solution (1 mL, 5%), and then subjected to a direct stream of concentrated sulfuric acid (5 mL). After cooling for 30 minutes, absorbance of 490 nm is measured. As shown in Table 2, concentrations of polysaccharides are calculated according to the standard curve.

Accordingly, the herbal extract of the invention is rich in triterpenes and polysaccharides, with the group A3 containing the highest amount of the active ingredients.

Trial (B): In Vitro Pharmacological Study of the Herbal Extract of the Invention MES-SA cells (human uterine sarcoma cell line) purchased from the Food Industry Research and Development Institute in Taiwan (BCRC 60333) is used in trial (B). The MES-SA cells are cultured in medium (McCoy's 5a) containing 10% FBS and 1.5 mM $_L$-glutamine. The MES-SA cells are incubated in an incubator with temperature of 37° C., $CO_2$ concentration of 5% and humidity of 95%. Medium used for culturing the MES-SA cells is renewed once in two days.

While subculturing, the MES-SA cells are centrifuged at 1,000 rpm for 5 minutes to remove supernatants, followed by mixing with fresh medium. The MES-SA cells preferably have a concentration of $1 \times 10^5$ to $1 \times 10^6$ cells/mL in 10 cm culturing dishes.

The culturing dishes 80 to 90% of bottom areas covered by the MES-SA cells are used in trial (B). Discolored medium is removed, 8 mL of PBS solution is used to wash the MES-SA cells and Trypsin/EDTA is added into the culturing dishes for 1 to 3 minutes. After the MES-SA cells dissociate with walls of the culturing dishes by slightly vortexing, the MES-SA cells are resuspended with prewarmed medium. The MES-SA cells are collected into centrifuge tubes, followed by centrifugation at 1,500 rpm for 10 minutes. Supernatants are removed and the MES-SA cells are resuspended in medium containing FBS. 20 μL of the MES-SA cells are collected, and 20 μL of trypan blue is added to the MES-SA cells for staining. The stained MES-SA cells are collected in cell counters, and numbers of the stained MES-SA cells are counted under microscope. Only the MES-SA cells with viability over 85% are suitable for the following experiments.

Concentrations of the MES-SA cells are adjusted to $1 \times 10^5$ cells/mL by medium containing FBS. 100 μL of the MES-SA cells with a concentration of $1 \times 10^4$ cells per are inoculated in a 96-well plate. The inoculated MES-SA cells are overnight cultured in an incubator with temperature of 37° C. and $CO_2$ concentration of 5%.

After culturing for 24 hours, the herbal extracts shown in Table 3 (in a concentration being 2 mg/mL, dissolved in DMSO) are added into each well of the 96-well plate. The MES-SA cells are overnight cultured in an incubator with temperature being 37° C. and $CO_2$ concentration being 5%.

After culturing for 24 hours, medium is removed, and the MES-SA cells are washed by a PBS solution. 100 µL of CCK-8 containing-fresh medium is added into each well of the 96-well plate. The MES-SA cells react with CCK-8 for 2 hours in the incubator (37° C., 5% $CO_2$), followed by vortexing for 5 minutes. Absorbance of 450 nm of the tumor cells in each well is detected.

TABLE 3 treatment used in trial (B) and survival rate thereof

| Groups | Treatment | Survival rate (%) |
|---|---|---|
| B0 | DMSO | 83.5 ± 0.4 |
| B1 | Group A1 | 28.1 ± 0.3 |
| B2 | Group A2 | 35.9 ± 0.2 |
| B3 | Group A3 | 15.2 ± 0.2 |

The survival rate shown in Table 3 is computed as followed:

Survival rate(%)=(Absorbance of a testing set/Absorbance of a control set)×100%

Referring to Table 3, the herbal extract according to preferred teachings of the present invention poses a better effect on inhibiting uterine sarcoma cell proliferation. Besides, since the herbal extract of group A3 shows the best effect, the following trial is performed using the herbal extract of group A3.

Trial (C): In Vivo Pharmacological Study of the Herbal Extract of the Invention

Wistar female rats (8 week-old, weight 180 to 190 grams) purchased from The National Laboratory Animal Center (NLAC) are used in trial (C). The rats are housed in an animal room in the Experimental Animal Center of Tajen university with constant temperature of 21±1° C. where is kept on a 12-hours light and 12-hours dark cycle. The rats are housed and kept on free diet and water.

The herbal extract of group A3 is orally administrated to the rats in a dosage of 300 mg per kilograms of the rats per day (group C1). Group C1 is a control set without the herbal extract (orally fed with RO water in a dosage being 10 mL per kilograms of the rats per day). At the same time, 200 mg of estrogen is administered via intraperitoneal injection. Weight, diet and water intake shown in Table 4 are recorded every day. Estrogen and progesterone levels are measured via celiac arterial bleeding 4 weeks later. Histologic specimens of uterus stained with Hematoxylin and eosin are shown as FIGS. 1 to 4.

With respect to Table 4, all of weight, diet intake and water intake show no significant difference between groups C0 and C1. However, estrogen and progesterone levels show significant decrease in group C1, with inhibition rates of estrogen and progesterone being 47.5±4.8% and 33.1±5.1%, respectively. That is, the herbal extract poses effect on decreasing estrogen and progesterone levels in vivo.

Figure 2:
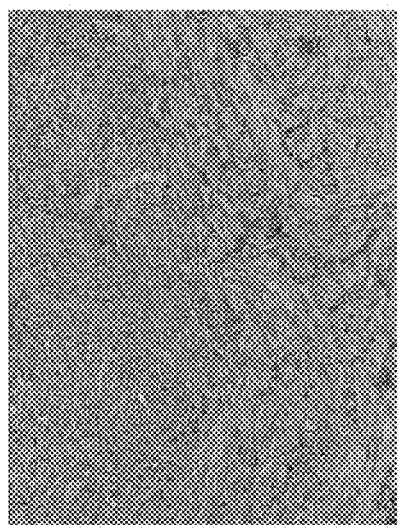
FIG. 2 depicts an H&E staining result of cornual obtained from group C0 rat.
Figure 3:
FIG. 3 depicts an H&E staining result of uterus obtained from group C1 rat.
Figure 4:
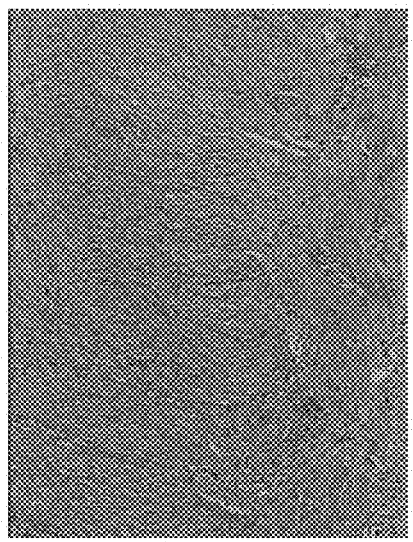
FIG. 4 depicts an H&E staining result of cornual obtained from group C1 rat.

Referring to FIGS. 1 and 2, smooth muscle cells of uterus show hypertrophy, eosin-stained cytoplasm, unclear cell boundary, disordered arrangement and no mitosis phenomena. That is, treatment of estrogen in trial (C) successfully induces uterine fibroids in rats. Moreover, as shown in FIGS. 3 and 4, the administered herbal extract can significantly reduce proliferation and hypertrophy of smooth muscle cells of uterus.

Accordingly, the herbal composition of the invention is rich in several active ingredients provided from *Antrodia cinnamomea*, *Astragalus membranaceus* and *Leonurus japonicus*, thereby posing synergistic effect on down-regulating estrogen and progesterone levels, decreasing growth of uterine fibroids.

Moreover, by administering the herbal extract of the invention containing abundant active ingredients provided from *Antrodia cinnamomea*, *Astragalus membranaceus* and *Leonurus japonicus*, the method of treating uterine fibroids can effectively inhibit growth of uterine fibroids, thereby preventing from painful menses and bleeding caused by uterine fibroids.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A method of treating uterine fibroids comprising administering an effective amount of an herbal extract to a subject in need thereof, wherein the herbal extract comprises extracts from *Antrodia cinnamomea*, *Astragalus membranaceus* and *Leonurus japonicas*; and wherein the herbal extract is produced by the steps of:

(a) blending by weight 25-75% fruiting bodies of *Antrodia cinnamomea*, 20-62.5%, roots of *Astragalus membranaceus*, and 4.2-12.5% ground portions of *Leonurus japonicas* to produce an herbal mixture, (b) mixing the herbal mixture with a 95% ethanol solution at a weight:volume ratio of 1:1 and extracting at 50-80° C. for 8-12 hours to produce an herbal solution, and

TABLE 4

Average weight, diet and water intake, and estrogen and progesterone levels of rats in trial (C) 28 days later

| Groups | Weight (g) | Diet intake (g/day) | Water intake (mL/day) | Estrogen level (ng/mL) | Progesterone level (ng/mL) |
|---|---|---|---|---|---|
| C0 | 234.5 ± 12.1 | 30.2 ± 3.1 | 33.2 ± 7.6 | 35066.1 ± 28.9 | 53.8 ± 4.7 |
| C1 | 258.3 ± 11.8 | 31.4 ± 2.9 | 33.8 ± 5.2 | 18386.7 ± 14.4 | 36.0 ± 4.4 |

(c) concentrating the herbal solution by vacuum filtration, vacuum concentration and/or freeze drying to obtain the herbal extract.

2. The method of treating uterine fibroids as claimed in claim 1, wherein the herbal extract is administered to the subject in need thereof in a dosage of 300 mg/per kilogram of body weight per day for 28 days.

* * * * *